United States Patent [19]

Poncy et al.

[11] 4,037,600
[45] July 26, 1977

[54] CATHETER PLACEMENT SYSTEM

[76] Inventors: Mark P. Poncy; George W. Poncy; Richard P. Poncy, all of 3670 E. Indus. Way, Riviera Beach, Fla. 33404

[21] Appl. No.: 595,014

[22] Filed: July 11, 1975

[51] Int. Cl.² .................. A61M 5/00; A61M 25/00
[52] U.S. Cl. .................. 128/214.4; 128/221; 128/348; 128/DIG. 16
[58] Field of Search ............ 128/214.4, 221, DIG. 16, 128/348–351

[56] References Cited

U.S. PATENT DOCUMENTS

| 2,820,457 | 1/1958 | Phillips | 128/351 |
| 3,185,151 | 5/1965 | Czorny | 128/214.4 |
| 3,241,554 | 3/1966 | Coanda | 128/350 R |
| 3,262,449 | 7/1966 | Pannier et al. | 128/214.4 |
| 3,399,674 | 9/1968 | Pannier et al. | 128/214.4 |
| 3,734,095 | 5/1973 | Santomieri | 128/214.4 |
| 3,739,778 | 6/1973 | Monestere et al. | 128/214.4 |
| 3,920,013 | 11/1975 | Bodzin | 128/214.4 |

FOREIGN PATENT DOCUMENTS

| 77,010 | 11/1948 | Czechoslovakia | 128/214.4 |
| 2,004,771 | 11/1969 | France | 128/214.4 |

Primary Examiner—Dalton L. Truluck
Attorney, Agent, or Firm—Lane, Aitken, Dunner & Ziems

[57] ABSTRACT

An intravenous catheter placement system in which a puncture needle and insertion catheter are disposed in guide passages formed in an easily handled blade-like body member. The body member is provided with guide track means cooperable with the needle in a manner to permit complete withdrawal and disposal of the needle after venipuncture to leave only the pliable insertion catheter remaining in the patient's vein. The needle may be either slotted to allow insertion of the catheter within the needle or provided with a pliable external sheath insertable with the needle and remaining after needle withdrawal to guide a small diameter insertion catheter for threading into the punctured vein. A catheter clamping means is provided to releasably retain the catheter against longitudinal movement in the body member which may be fixed to the exterior of the patient's body by a strap connected to the body or by taping.

13 Claims, 8 Drawing Figures

CATHETER PLACEMENT SYSTEM

BACKGROUND OF THE INVENTION

This invention relates to a catheter inserting apparatus and, more particularly, it concerns an improved catheter-needle handling device by which a hollow or tubular needle used for penetrating to the interior of a blood vessel may be completely removed to leave only a relatively soft catheter remaining in the blood vessel as a conduit by which fluid may be passed between the blood vessel and an external receptacle.

The use of intravenous systems by which fluids are passed directly between a patient's bloodstream and an external receptacle by flexible tubing is well known in the practice of medicine. Most commonly, such intravenous systems involve a direct and essentially permanent connnection of the tubing to a rigid tubular needle having a sharpened point for direct insertion through the patient's flesh and into a blood vessel from or to which fluid is withdrawn on introduced. Where the intravenous system is to be used for an indeterminate period of time, such as during the administration of drugs or nurishment directly into the patient's circulatory system, the needle is taped or otherwise fixed against movement to avoid injury resulting from relative movement between the needle and the portion of the patient's anatomy in which the needle is lodged. The major difficulty with such systems is that obviously, the sharpness of the needle point required for effective venipuncture remains to repuncture the veseel and surrounding tissue to cause not only undesirable local injury in the vincinity of the punctured blood vessel, but often a more serious injury as a result of inflation of fluids to the tissues surrounding the blood vessel.

To circumvent this base difficulty, systems are now available which permit withdrawal of the needle from the body following venipuncture to leave only a relatively soft plastic catheter in the blood vessel. Of such systems which are available commercially, the catheter is positioned initially in concentric relation with the needle, either directly within a relatively large diameter needle or on the exterior of the smaller needle as an outer sheath. Where the catheter is initially positioned within the needle, the removal of the needle following the venipuncture is along the length of the catheter. Although complete removal of the needle from the catheter extending to the exterior of the patient's body would appear possible, the provision of enlarged diameter coupling or valving sections along the length of the catheter prevents this in practice. As a result, the needle in such systems is usually withdrawn only partially along the length of the inserted catheter and anchored to the patient's body while it remains surrounding the catheter tube. While the likelihood of direct danger of the patient is reduced substantially, the needle can and often does cause an unwanted restriction of the fluid conduit provided by the catheter and may even puncture the catheter.

In those commercially available systems where the needle is initially positioned within the catheter, the exterior end of the catheter must be open to permit needle withdrawal. In particular, needle withdrawal is effected by a thin wire stylus extending the length of the catheter to facilitate removal by pulling the stylus from the exterior end of the catheter. Such an arrangement is undesirable from the standpoint of contamination inasmuch as a direct channel exists for an unwanted period of time between the outside environment and the patient's circulatory system.

Further attempts at catheter insertion or placement systems in which provision is made for needle removal following venipuncture are represented by the disclosures of U.S. Pat. No. 3,399,674 issued Sept. 3, 1968 to K. A. Panier et al and U.S. Pat. No. 3,739,778 issued June 19, 1973 to Martin Monestere, Jr. et al. In the Panier et al patent, a relatively short length of small diameter catheter extends from an exterior juncture with a thick walled tube into a slotted exterior needle oriented at an angle with respect to the exterior tube. After venipuncture, the needle is withdrawn to leave only the small diameter catheter within the blood vessel by virtue of the needle slot extending from the initial juncture with the catheter throughout its length to the pointed end thereof. In the Monestere, Jr. et al patent, the needle initially extends through a sheath of catheter material inserted and left remaining within the patient's blood vessel. After withdrawal of the needle following venipuncture, a small diameter catheter is fed through the needle sheath into the blood vessel through a flexible exterior housing joint.

Although the disclosures of both the Panier et al and Monestere, Jr. et al patents represent catheter insertion systems by which complete removal of a venipuncture needle is facilitated after the catheter placement, neither disclosure takes into account the need for a positive guiding or tracking of the catheter after removal of the needle. It is often necessary, for example, to advance a small diameter catheter along a blood vessel for a length considerably in excess of the length of a venipuncture needle. Because of the extremely small diameter of the catheter and the requirement that it be pushed longitudinally at a point spaced from the end extending within the patient's body, any resistance to longitudinal feeding or threading in this manner will result in a collapse unless the catheter is guided along its length in advance of the point at which the pushing force is applied. Also, it will be appreciated that breakage or severance of the catheter portion within the patient's circulatory system must be avoided whether such breakage is as a result of catheter manipulation after venipuncture or during removal of the puncture needle.

SUMMARY OF THE INVENTION

In accordance with the present invention, the problems heretofore experienced with placement and use of intravenous catheters are substantially mitigated by a needle-catheter tracking device in which manipulation of a puncture needle and pliable intravenal catheter is facilitated during venipuncture, needle withdrawal and catheter threading and by which positive retention of intravenal catheter position is assured. Although the invention contemplates various structural embodiments, the tracking device is preferably formed as a flattened, blade-like body having a tapered end facing in the direction of needle-catheter insertion and terminating rearwardly in a relatively wide linear edge thereby to provide a configuration which may be easily handled, positively oriented both longitudinally or in the direction of needle-catheter insertion as well as angularly with respect to the needle orientation on its axis and easily secured after catheter placement to a limb or other portion of the patient's anatomy by strapping or tape. The forward portion of the body is formed with a longitudinal and linear guiding passage adapted to receive a puncture needle extending from a pointed puncture end to a rearwardly disposed hub which may be grasped for withdrawal of the needle independently of the spade-shaped body following venipuncture. The hub is slidably disposed in an elongated track formed in the body member to assure complete linear and angular orientation of the needle during withdrawal. A curved guiding passage opens at the rear edge of the body member and extends forwardly to a tangential merger with the linear guiding passage for directing an insertion catheter along an axis concentric with the axis of the needle. The curved catheter guide passage is provided at its exit from the rear end of the body with a boss portion forming part of a catheter clamping means supported directly by the body member and by which the catheter may be retained or locked against longitudinal movement in the body member. The locking device also preferably carries a sterile envelope in which the catheter is initially packaged and by which complete sterilization may be maintained throughout the catheter placement operation.

In one embodiment of the invention, the needle is longitudinally slotted from its insertion point rearwardly to the point of its intersection with the curved passageway in the body member so that the insertion catheter, initially positioned within the needle, will remain within the patient's blood vessel after venipuncture and rearward withdrawal of the needle. In an alternative embodiment, the puncture needle extends through an insertable sheath which remains after venipuncture as a shortened pliable portion through which a small diameter catheter may be fed for any desired distance along the blood vessel in which the sheath is positioned.

Among the objects of the present invention are therefore: the provision of an improved intravenous catheter placement device; the provision of such a device by which positional control over both a puncture needle and catheter feeding or threading is maximized; the provision of such a device which enables fluid connection of an insertion catheter to an external fluid receptacle either before or after venipuncture; the provision of such a device which enables insertion and use under conditions in which sterilization is optimized; the provision of a device of the type referred to by which the potential for catheter breakage after insertion is reduced to an absolute minimum; the provision of a catheter placement device of the type referred to by which anchorage of an insertion catheter to an exterior portion of the patient's body is greatly facilitated; and the provision of such a device by which a flashback indication of completed venipuncture is available.

Other objects and further scope of applicability of the present invention will become apparent from the detailed description to follow taken in conjunction with the accompanying drawings wherein like reference numerals designate like parts.

DETAILED DESCRIPTION OF THE PREFERRED EMBODIMENTS

Figure 1:
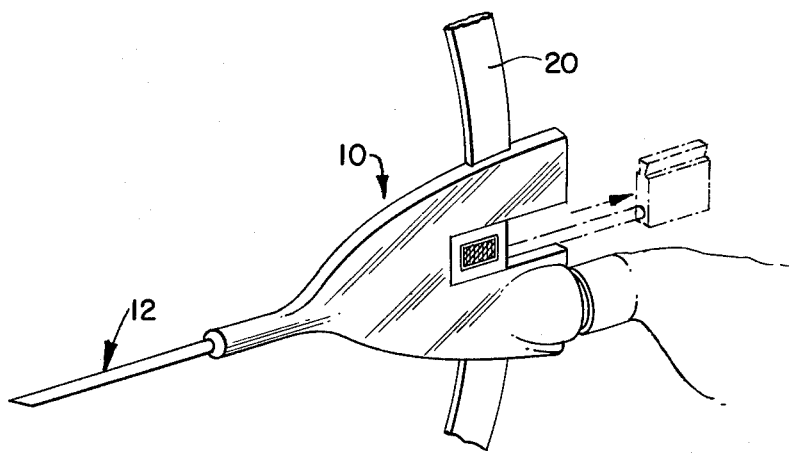
FIG. 1 is a perspective view illustrating the catheter placement device of the present invention.

In FIGS. 1–6 of the drawings, one embodiment of the present invention is shown to include a tracking body member, generally designed by the reference numeral 10, initially supporting a venipuncture needle 12 and an insertion catheter 14. As illustrated most clearly in FIGS. 1–3 and 6, the tracking body member 10 is of generally blade-like configuration having a tapered forward end 16 which diverges rearwardly to a planar and generally rectangular rear edge surface 18. The generally flat configuration of the body member 10 facilitates the securement to an exterior portion of a patient's anatomy either by a bracelet-like strap 20 as shown in FIG. 1 or by the use of adhesive tape in accordance with conventional practice. Although the body member may be formed from any suitable materials, a transparent plastic material is preferred to facilitate visual observation of all portions of the needle 12 and catheter 14.

Figure 2:
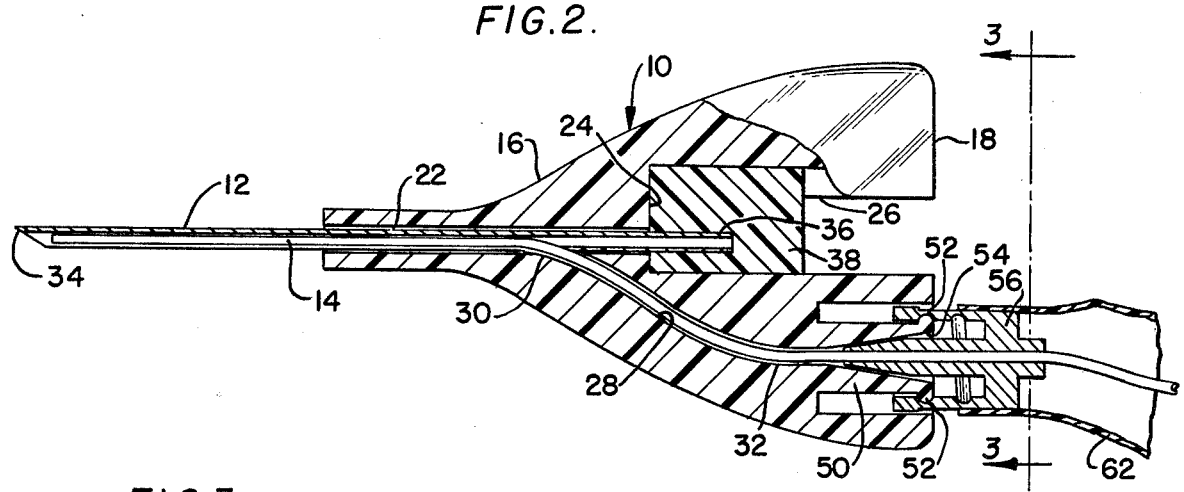
FIG. 2 is an enlarged side elevation in partial cross-section of the embodiment illustrated in FIG. 1.
Figure 3:
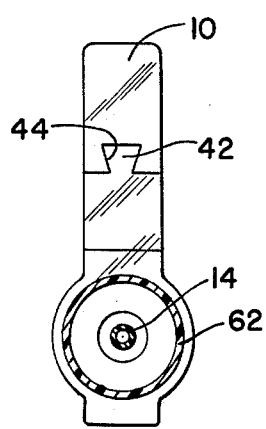
FIG. 3 is a cross-section taken on line 3—3 of FIG. 2.
Figure 4:
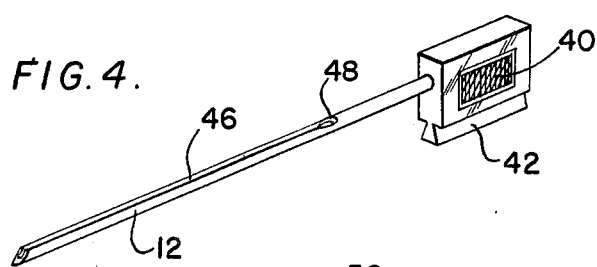
FIG. 4 is a perspective view illustrating the puncture needle of the embodiment of FIG. 1.
Figure 5:
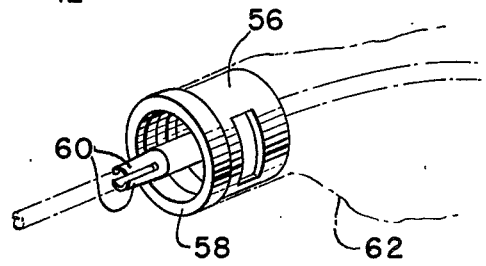
FIG. 5 is an enlarged fragmentary perspective view illustrating an insertion catheter locking component of the present invention.
Figure 6:
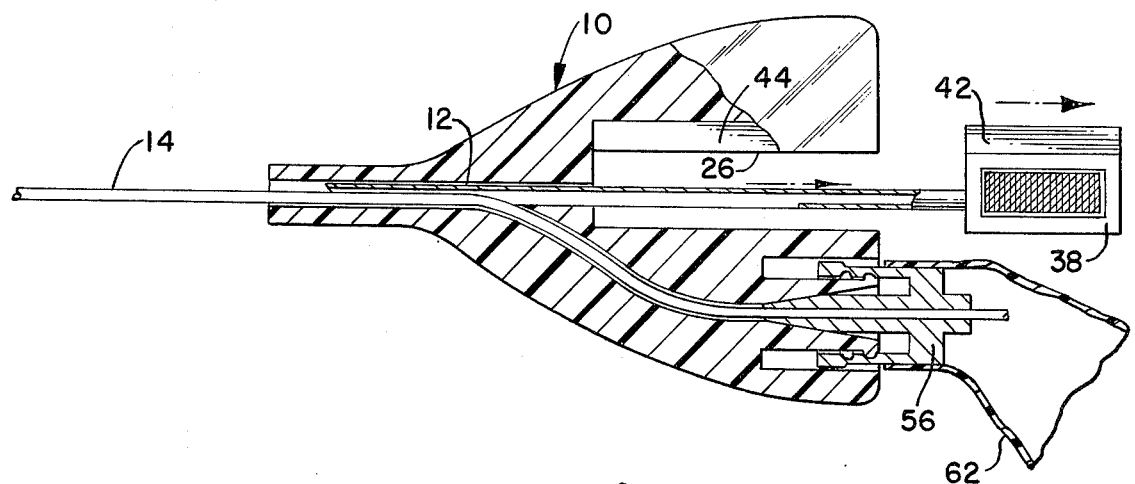
FIG. 6 is a side elevation in parallel cross-section similar to FIG. 2 but illustrating the needle component partially withdrawn after venipuncture.

As shown most clearly in FIGS. 2 and 6 of the drawings, the forward end portion of the body member 10 is formed having a longitudinal and linear guiding passage 22 of a diameter to provide a close sliding fit with the exterior of the puncture needle 12. The passage 22 extends from the forward end of the body member 10 rearwardly through a forward abutment surface 24 of a hub guiding track 26 which, in turn, opens through the rearward edge 18 of the body member as shown. The interior of the body member 10 is provided with a further curved guiding passage 28 having a pair of reverse bends or curves 30 and 32 through which the flexible catheter 14 extends.

The needle 12 is provided at one end with a sharpened puncture 34 and is embedded at its other end 36 in a block-like hub 38 so as to be fixed against relative longitudinal and rotational movement with respect to the block 38. The block 38 is provided on opposite sides with knurled gripping surfaces 40 by which it may be grasped and handled independently of the body member 10. In the embodiment of FIGS. 1–6, the hub block is provided with an undercut ridge or dovetail 42 engageable in a complementing undercut groove 44 in the guide track 26. Thus, it will be appreciated that any movement of the needle 12 effected by relative movement of the hub 38 along the track 26 will be without angular repositioning of the needle.

In the embodiment of FIGS. 1–6, the needle 12 is provided with a slot 46 extending from its sharpened tip 34 rearwardly to an enlargement of the slot or opening 48. The opening 48 is oriented with respect to the hub 38 such that when the hub is inserted against the abutment surface 24, the opening 48 becomes aligned with the curved guide passage 28, thereby enabling the catheter 14 to extend through the opening 48 and along the slotted portion of the needle 12 in concentric relation. The inside diameter of the needle corresponds closely to the outside diameter of the catheter 14 whereas the effective width of the slot 46 in the needle is slightly less than the outside diameter of the catheter. As a result, the catheter 14 will be retained concentrically within the slotted portion of the needle, such as during venipuncture, but will make possible the withdrawal of the needle 12 as the result of a slight temporary compression of the catheter as the needle is withdrawn.

Although retrograde or withdrawing longitudinal movement of the catheter 14 on rearward withdrawal of the needle 12 in the embodiment of FIGS. 1-6 will be prevented in substantial measure by the curved guiding passage 28 and the restriction it provides to rearward movement of the catheter, further provision is made for locking the catheter 14 against longitudinal movement relative to the body 10. In particular, the curved catheter guide passage 28 opens to the rear edge surface 18 of the body member through a circlar boss portion 50 having exterior threading lugs 52 and a conical or tapered interior surface 54. As shown most clearly in FIGS. 2 and 5 of the drawings, a catheter clamp 56 is rotatably positioned about the catheter 14. The clamp 56 is formed having an interiorly threaded skirt portion 58 and a central portion establishing externally tapered clamping jaws 60. The exterior taper of the clamping jaws 60 generally complements the conical surface 54 such that axial movement of the clamp 56 as a result of the threading of the lugs 52 within the interiorly threaded skirt 58 will cause the jaws 62 to frictionally engage the catheter 14. The exterior cylindrical surface of the clamp 56 serves further to mount a sterile bag or envelope 62 in which the end of the catheter 12 projecting rearwardly from the body member 10 may be housed.

In the use of the embodiment illustrated in FIGS. 1-6, it will be appreaciated that the assembly of the body 10, the needle 12 and the insertion catheter 14 will be essentially as illustrated in FIGS. 1 and 2 of the drawings. A sterile cover for the needle 12 and the portion of the catheter 14 projecting from the forward end of the body will be supplied in accordance with conventional practice. In the event the catheter insertion is to be used to supply a therapeutic fluid from an external source or receptacle (not shown), the external receptacle is first connected by way of flexible tubing to a socket connector (not shown) on the end of the insertion catheter 14 within the sterile envelope 62. After a shot of the therapeutic fluid is passed through the catheter for sterilization purposes and to eliminate air from the catheter, the needle is inserted into a blood vessel of the patient to place the end of the insertion catheter 14 within the needle 12 in fluid communication with the patient's blood vessel. Thereafter, the body member 10 may be held temporarily to the exterior of the patient's anatomy where the venipuncture is made and the clamping device 56 manipulated to restrain the catheter 14 against longitudinal movement with respect to the body. Thereafter, the needle 12 may be removed by grasping the narrowed surface portions of the hub 38 and the hub withdrawn to remove the needle completely from the patient's blood vessel as well as from the body member 10. The body member 10 is then secured either by using the strap 20 or by tape.

Should it be desired to advance the catheter 14 within the patient's blood vessel, this may be done either before or after needle withdrawal merely by pushing the catheter along the guide passage 28 with the clamp 56 in a released condition. Because of the curved guide passage 28, any unwanted distortion or bending in the catheter during such threading advance will occur only between the point at which pushing pressure is exerted and the rear end of the body member where it may be clearly observed and corrected. Such threading of the catheter 14 is greately facilitated by the parallel orientation of the catheter and the axis of needle insertion at least over the portion of the catheter emerging rearwardly of the body 10. Also, it is important to note that because the needle 12 is restrained against angular movement by the track 26 in the body member 10, the potential for severance of the catheter 14 during the passage of the needle slot 46 is eliminated.

Figure 7:
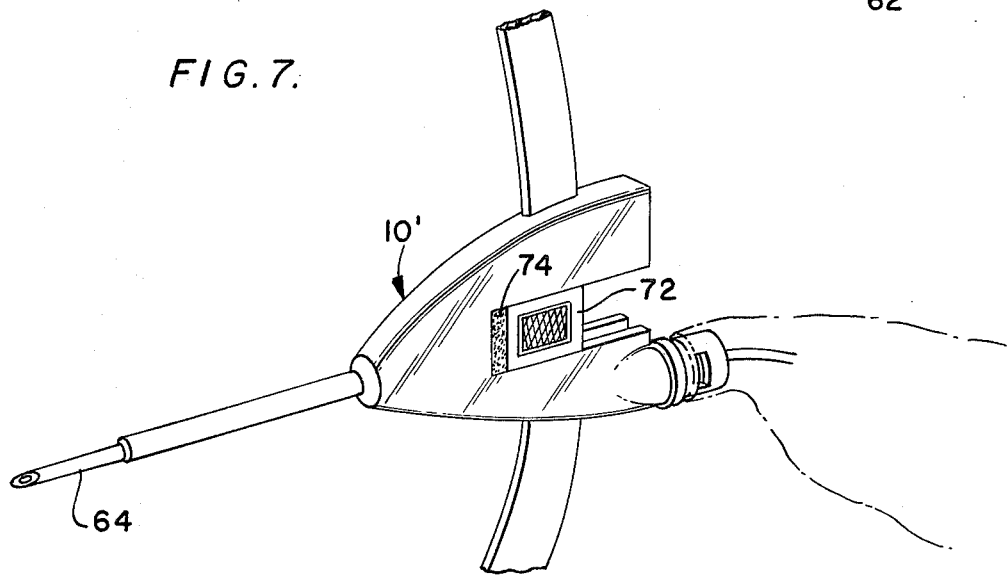
FIG. 7 is a perspective view illustrating an alternative embodiment of the invention.
Figure 8:
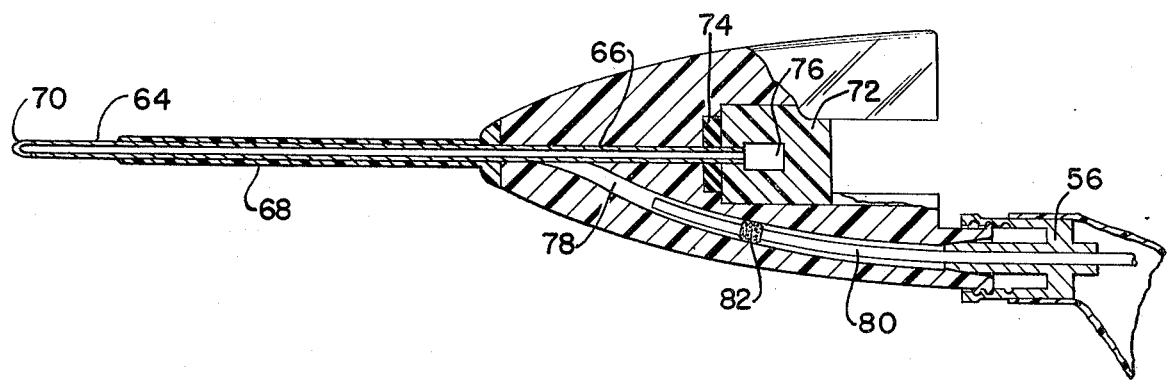
FIG. 8 is an enlarged side elevation in parallel cross-section illustrating the embodiment in FIG. 7.

In an alternative embodiment of the invention illustrated in FIGS. 7 and 8 of the drawings, a body member, generally designated by the reference numeral 10', is provided having an external configuration resembling the body member of the previous embodiment. In this instance, however, a closed tubular needle 64 is employed for venipuncture and is initially disposed in the body member 10' along a linear guide passage 66 and through a flexible outer sheath 68 to be inserted with the needle to the interior of a patient's blood vessel, for example. The needle 64 extends from a sharpened puncture point 70 rearwardly through the sheath 68 and guide passageway 66 for anchorage in a hub block 72. A self-sealing elastomeric plug is positioned in front of the block 72 such that upon withdrawal of the needle 70, the guide passageway will be sealed at its rear end. Also, it will be noted that the open rear end of the needle 64 communicates with a small chamber 76 in the block 72 which, being of clear or transparent plastic, will enable a flashback of blood into the chamber 76 to be observed thrugh the hub block 72. The flashback will indicate that venipuncture is completed.

A curved guide passageway 78 is again provided as in the previous embodiment to merge with the linear passageway 66 so that an insertion catheter 80 may be fed into the linear guide passageway 66 through the sheath 68 into a blood vessel though in this instance, only after the needle 64 has been removed. A small gasket 82 is provided in the channel 78 around the catheter 80 to provide the flashback of blood from escaping out through the channel 78. The gasket should be constructed of a material such as closed cell foam to maintain a seal while providing low friction on the catheter so that the catheter can slide easily through the gasket 82. Alternatively, a thin walled latex gasket anchored in the body member 10 may be used. The insertion catheter clamp 56 is also provided so that full control over longitudinal positioning of the catheter 80 is accounted for.

Use of the embodiment illustrated in FIGS. 7 and 8 will be appreciated as departing only slightly from the use of the embodiment illustrated in FIGS. 1-6. In other words, after venipuncture, the needle 62 must be fully withdrawn prior to advancing movement of the insertion catheter 80. Also in this embodiment, it is possible to administer fluid intravenously by using only the sheath 68 to establish the fluid communication with the blood vessel interior. In other words, advancing the insertion chamber 80 beyond the position illustrated in FIG. 8, for example, is necessary only if a longer length of inserted catheter is needed.

Thus, it will be appreciated that by this invention there is provided an improved catheter insertion apparatus by which the above mentioned objectives are completely fulfilled. Although alternative preferred embodiments of the invention have been illustrated and described herein, other embodiments are contemplated as well as modifications and/or variations in the disclosed embodiments. It is expressly intended, therefore, that the foregoing description is illustrative only of preferred embodiments and that the true spirit and scope of the present invention be determined by reference to the appended claims.

We claim:

1. Catheter placement apparatus comprising:
   a body member with front and rear ends having a linear guiding passage extending longitudinally therein and a smoothly curved guiding passage merging with said linear guiding passage within said body member and opening through the rear end of said body member in essentially parallel relationship to said linear guiding passage;
   a venipuncture needle slidable received in said linear guiding passage, said needle having a puncture point at one end projecting from said body member at the front end and a hub block fixed at the opposite end of said needle;
   an insertion catheter positioned in said curved guiding passage and being normally slidable through said curved guiding passage and into said linear guiding passage.

2. The apparatus recited in claim 1, wherein said needle is formed with a slot extending from said puncture point to an opening established as a terminal enlargement in said slot, said opening being initially positioned at the merger of said linear and curved guiding passages, said catheter extending through said opening and within said needle along said slot.

3. The apparatus recited in claim 1, wherein said needle is a closed tube from said puncture point to said hub block and including a pliable sheath extending from said body member toward puncture point on the exterior of said needle and concentric therewith, said sheath being insertable with said needle.

4. The apparatus recited in claim 3, including an elastomeric seal to close the end of said passageway adjacent to said hub block upon withdrawal of said needle.

5. The apparatus recited in claim 4, wherein said hub block is formed of a transparent material and with a chamber at the end of said needle extending within said hub block to provide a flashback indication of venipuncture completion.

6. The apparatus recited in claim 3, further comprising a gasket in said curved guiding passage, said catheter extending through said gasket and being slidable with respect to said gasket.

7. The apparatus recited in claim 6, wherein the material of said gasket comprises closed cell foam.

8. The apparatus recited in claim 1 wherein said body member has a flat blade-like shape, the apparatus further comprising a fastening strap connected to said body member for attaching said body member inmovably to a surface to which venipuncture is made.

9. Apparatus for inserting a catheter comprising:
   a rigid body member having front and rear ends;
   a linear guiding passage extending through said body member for receiving a hollow needle;
   a curved guiding passage formed in said body member, said curved guiding passage merging with said linear guiding passage within said body member and extending from the rear end thereof in an essentially parallel spaced relation with respect to said linear passage;
   releasable catheter clamping means supported by said body member at the rear end thereof about said curved guiding passage to lock a catheter in said curved passageway against lonigitudinal movement with respect to said body member; and
   means defining a needle tracking guideway in said body member by which the linear and angular orientation of a hollow needle may be fixed with relation to said body member.

10. The apparatus recited in claim 9, wherein said releasable clamping means comprises boss means at the rear end of said body having external lugs and internal tapered surface concentric with said curved guiding passage, and an internally threaded clamp engageable with said lugs and having externally tapered flexible jaws movable by said internal tapered surface into clamping engagement with a catheter positioned within said curved guiding passage.

11. The apparatus recited in claim 10, wherein said clamp supports a sterile envelope to enclose a catheter extending within said curved passageway 12. Catheter placement apparatus comprising:
   a body member with front and rear ends having a linear guiding passage extending longitudinally therein and a smoothly curved guiding passage merging with said linear guiding passage within said body member and opening through the rear end of said body member in essentially parallel relation to said linear guiding passage;
   a venipuncture needle slidably received in said linear guiding passage, said needle having a puncture point at one end projecting from said body member at the front end and a hub block fixed at the opposite end of said needle;
   means defining a hub block track in said body member to accommodate linear movement of said hub block towards said rear end of said body member for withdrawal of said needle from said body member in constant angular orientation;
   an insertion catheter positioned in said curved guiding passage; and
   means to clamp said catheter releasably against longitudinal movement in said body member, said catheter being slidable through said curved guiding passage and said linear guiding passage except when clamped by said clamping means.

13. The apparatus recited in claim 12, wherein said releasable clamp means comprises boss means at said one end of said body member having external lugs and an internal tapered surface concentric with said curved guiding passage, and an internally threaded clamp engageable with said lugs and having externally tapered flexible jaws movable by said internal tapered surface into clamping engagement with said surface.

* * * * *

UNITED STATES PATENT OFFICE
CERTIFICATE OF CORRECTION

Patent No. 4,037,600  Dated July 26, 1977

Inventor(s) Mark P. Poncy et al

It is certified that error appears in the above-identified patent and that said Letters Patent are hereby corrected as shown below:

Column 1, line 8, "penetrating" should read --penetration--;

line 34, "inflation" should read --infiltration--;

line 36, "base" should read --basic--.

Column 4, line 6, "parallel" should read --partial--;

line 43, after the word "puncture", the word --point-- should be inserted.

Column 5, line 15, "circlar" should read --circular--.

Column 6, line 59, "chamber" should read --catheter--.

Signed and Sealed this

Eighth Day of November 1977

[SEAL]

Attest:

RUTH C. MASON
Attesting Officer

LUTRELLE F. PARKER
Acting Commissioner of Patents and Trademarks